United States Patent [19]

Adams et al.

[11] Patent Number: 4,552,723

[45] Date of Patent: Nov. 12, 1985

[54] LC/FTIR SYSTEM WITH THERMOSPRAY SOLVENT SEPARATION

[75] Inventors: Gary E. Adams, Danbury; John M. Casper, Brookfield, both of Conn.; Roy J. Gritter, San Jose, Calif.

[73] Assignee: International Business Machines Corporation, Armonk, N.Y.

[21] Appl. No.: 519,273

[22] Filed: Aug. 1, 1983

[51] Int. Cl.[4] .................. G01J 1/00; G01N 21/13; G01N 30/02

[52] U.S. Cl. .................. 422/66; 73/61.1 C; 250/338; 356/36; 356/346; 422/70; 422/91; 436/44; 436/161

[58] Field of Search .......... 422/66, 70, 91; 436/44, 436/46, 161, 162, 164; 73/61.1 C, 61.3; 250/338, 341; 356/346, 36

[56] References Cited

U.S. PATENT DOCUMENTS

| | | | |
|---|---|---|---|
| 3,667,917 | 6/1972 | Brandt | 436/44 |
| 3,904,364 | 9/1975 | Dodson | 436/155 |
| 4,055,987 | 11/1977 | McFadden | 422/70 |
| 4,056,969 | 11/1977 | Barringer | 422/70 |
| 4,420,566 | 12/1983 | Jessop et al. | 436/46 |

OTHER PUBLICATIONS

Blakely et al., Analytical Chemistry, vol. 52, No. 11, Sep. 1980, pp. 1636-1641.
Amino Acid Analysis, J. M. Rattenbury, 1981, pp. 16-18.
"The Estimation of the Leucine Isomersion Protein Hydrolysates by Infrared Analysis" by S. E. Darmon et al., Biochemical Journal, vol. 42, 1948, pp. 508-516.

Primary Examiner—Barry S. Richman
Assistant Examiner—C. M. Delahunty
Attorney, Agent, or Firm—Douglas R. McKechnie

[57] ABSTRACT

Effluent from an LC is passed through a thermospray nozzle which flash vaporizes substantially all of the solvent while directing any sample components as a collimated beam onto a moving tape so that the various components form spots on the tape. The tape is moved along a path that intercepts the optical path of an FTIR spectrometer whereby IR energy from the spectrometer is passed through each sample component and is then spectrally analyzed. The tape can be wound up, stored, and later used for further analysis of the spots, as desired, in the FTIR spectrometer.

5 Claims, 2 Drawing Figures

LC/FTIR SYSTEM WITH THERMOSPRAY SOLVENT SEPARATION

FIELD OF THE INVENTION

This invention relates to an analytical instrument system method and apparatus in which the output from a liquid chromatograph (LC) is fed through a thermospray solvent separator so as to deliver sample constituents to a Fourier transform infrared (FTIR) spectrometer for analysis.

BACKGROUND OF THE INVENTION

Liquid chromatography and FTIR spectrometry separately and in combination are well known analytical techniques. In liquid chromatography, a sample and a solvent are pumped through an LC column which separates the sample into its constituents or components causing them to flow out of or efflux from the LC at different times. The effluent passes through a detector which produces a signal that can be recorded as a chromatogram. The signal associated with the components produce peaks and the components from the LC are sometimes called "eluting peaks". While a chromatogram provides information useful for analyzing the sample components, it is sometimes desirable to further analyze eluting peaks by FTIR spectrometry.

In FTIR spectrometry, IR energy from an interferometer irradiates a sample which absorbs some of the energy at different wavelengths. The remaining energy is detected to produce a composite time domain signal called an interferogram. Such signal is digitized and subjected to mathematical analysis including a Fourier transform, to produce an absorption spectrum indicative of the structure and make-up of the sample. By combining this technique with that of liquid chromatography, the FTIR method provides further information about the molecular character of each eluting peak.

When such techniques are combined, it is desirable to analyze the eluting peaks on a real time basis, i.e., as they flow from the LC. But this objective is difficult to achieve primarily because of the presence of a large amount or excess of solvent in the effluent. Generally, the excess solvent must be removed in order to provide an accurate analysis.

Another general characteristic of prior art techniques is that the effluent from the LC, after passing through a detector, is normally collected in a waste receptacle and disposed of. The investigator cannot at a later time go back and test the original sample but would have to repeat the experiment and hope that the results reproduce the original measurements.

A technique called "thermospraying" was also developed in the prior art for removing excess amounts of solvent from the effluent from an LC and directing the remainder, including any eluting peaks or components, into a mass spectrometer where the components are ionized and analyzed. This technique is described in "Liquid Chromatograph - Mass Spectrometer for Analysis of Non-Volatile Samples" by C. R. Blakely, J. J. Carmody, and M. L. Vestal, Anal. Chem., 1980, Vol. 52, pages 1636–1641. The liquid flowing from the LC is passed through a flash vaporizer in which about 95% of the liquid is vaporized while the remainder, including the non-volatile sample components, are directed as a collimated particle or aerosol beam moving at a rapid velocity, into the mass spectrometer for ionization and analysis. As described in the article, the vaporizer is an oxy-hydrogen torch through which the effluent passes. Subsequently, an electrically heated nozzle was developed to replace the torch.

SUMMARY OF THE INVENTION

Accordingly, one of the objects of the invention is to provide an LC/FTIR analytical system in which effluent from the LC is analyzed on a real time basis by an FTIR spectrometer.

Another object of the invention is to adapt the thermospray technique previously used in connection with a mass spectrometer, to remove excess amounts of solvent from the effluent from an LC as a prelude to introducing the sample components into an FTIR spectrometer.

Still another object of the invention is to non-destructively analyze sample components and to collect and store the sample components from an LC for archival purposes allowing a later retrieval of individual components and analysis thereof.

Briefly, in accordance with the invention, effluent from an LC is passed through a thermospray nozzle which flash vaporizes substantially all of the solvent while directing any sample components as a collimated beam onto a moving tape so that the various components form spots on the tape. The tape is moved along a path that intercepts the optical path of an FTIR spectrometer whereby IR energy from the spectrometer is passed through each sample component and is then spectrally analyzed. The tape can be wound up, stored, and later used for further analysis of the spots, as desired, in the FTIR spectrometer.

Other objects and advantages of the invention will be apparent from the following description, taken in connection with the accompanying drawing wherein.

Figure 1:
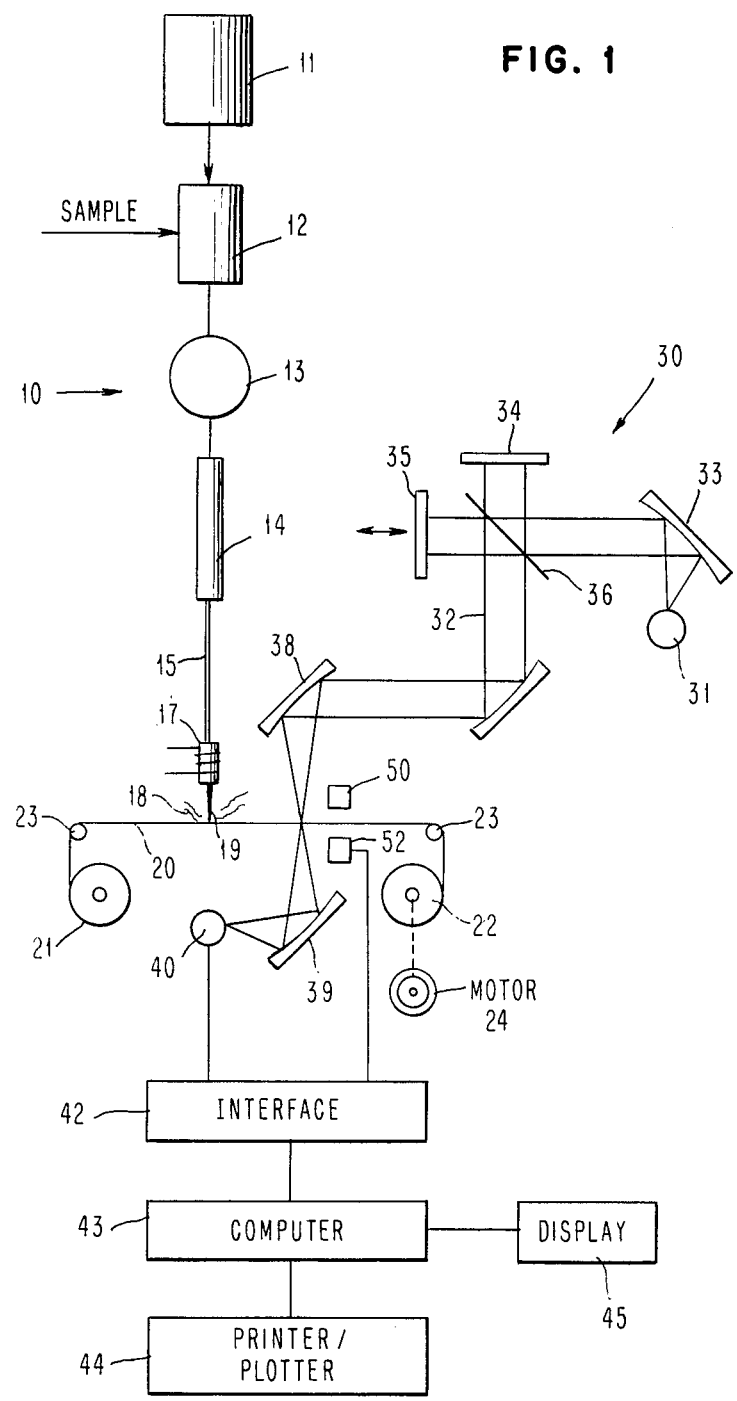
FIG. 1 is a schematic view of an FTIR/LC system embodying the invention.

Referring now to the drawings and first to FIG. 1, an LC system 10 includes a solvent reservoir 11 connected to an injector 12 through which a sample is introduced into the flowing solvent. The combined solvent and sample are pumped by pump 13 through an LC column 14 where the sample is separated into its constituents in accordance with well known principles of liquid chromatography. Column 14 is connected to a tube 15 which conducts the effluent from column 14 into a thermospray vaporizer 17. Vaporizer 17 is operative to separate the solvent 18 from the effluent by the flash vaporization thereof while allowing any sample component 19 to be directed or sprayed onto a moving tape 20. A suitable LC for performing such function is the type 9533 Liquid Chromatograph commercially available from IBM Instruments, Inc., Danbury, Conn.

Tape 20 forms part of a tape transport system that includes a supply reel 21, a take-up reel 22, and idler pulleys or wheels 23 which guide tape 20 past the vaporizer. A motor 24 drives take-up reel 22 so as to move tape 20 at a constant velocity.

An FTIR spectrometer 30 includes a broad band source 31 of infrared energy which is directed along an optical path 32 to detector 40. From source 31, IR energy is collimated by a parabolic mirror 33 and directed into a Michaelson interferometer including a fixed mirror 34, movable mirror 35 and beam splitter 36. The energy is then directed by a parabolic mirror 37 to a focusing mirror 38 that focuses the beam on the surface of tape 20. The beam passes through the tape and is directed by a focusing mirror 39 onto a detector 40 that produces electrical signals proportional to the strength of the beam received thereby. The output of detector 40 is fed through an interface 42 that includes conventional amplifiers, A/D converters, etc. and into a computer 43 for storage and analysis. A printer/plotter 44 and display 45 are connected to computer 43 allowing the results to be plotted, printed or displayed. A suitable spectrometer for performing these functions is the IR32 spectrometer commercially available from IBM Instruments, Inc., Danbury, Conn.

In the embodiment of FIG. 1, tape 20 is substantially transparent to the passage of IR energy and thus operates in the transmission mode where the energy passes through both a sample spot on the tape and the body of the tape. As an alternative, the system can be arranged in a reflective mode such as that shown in FIG. 2 where the tape is reflective of the IR energy. For example, a metalized tape can be used with the sample components being deposited as spots 19A–19C on the surface of the metal so that the IR energy passes through a spot, and is reflected from the surface back through the spot, towards the detector. In other words, in the reflective mode, the material of the body of the tape does not interfere with the IR energy and the signals from the spot are stronger to the extent that the IR energy passes twice through a sample spot.

Means are also provided allowing the location of any given spot on tape 20 to be identified. To this end, tape 20 is provided with a series of sprocket holes 48. Tape 20 is opaque or partially opaque to the light from sensor 50. A light source 50 is arranged on one side of the tape and directs light towards the path of travel of sprocket holes 48. A light detector 52 is positioned on the other side of the tape so that as the sprocket holes pass between source 50 and detector 52, light passes through such holes producing an electrical signal that allows the sprocket holes to be counted. The sprocket holes are located a known distance D1 apart so that the distance from a starting point, such as the beginning of the tape, can be readily determined by simply counting the number of holes that have passed. The output of detector 52 is also fed through interface 42 including any necessary amplifiers, counters, etc., to the computer which then can be used to equate the location of any particular spot with its location on the tape. The location of source 50 and detector 52 could be right along side where the IR energy hits the tape or it can be displaced a known distance D2 therefrom. As shown, this displacement is forward of the point at which the spot is actually analyzed so as to introduce a slight delay between when a particular hole 48 is encountered and when a spot associated therewith is analyzed.

Figure 2:
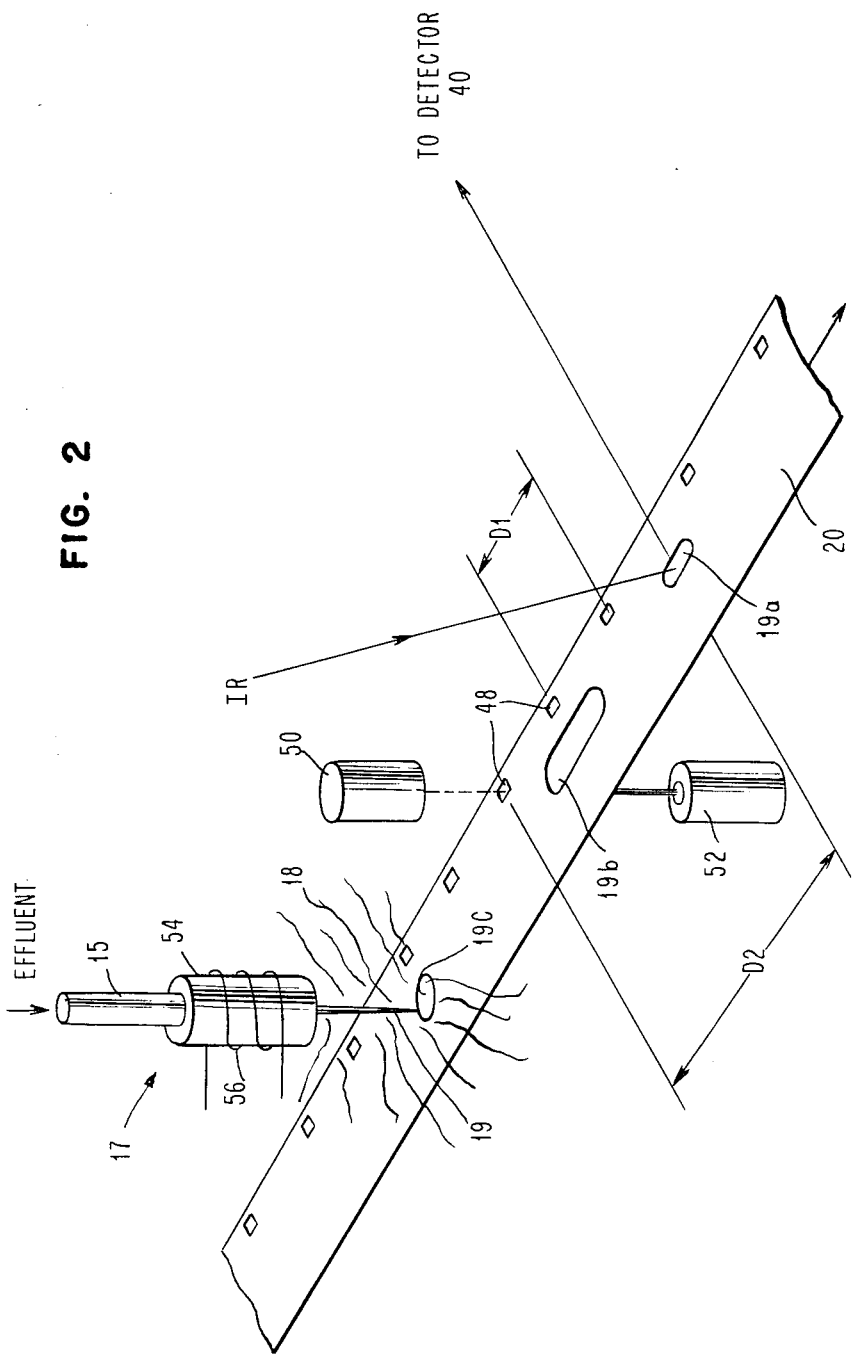
FIG. 2 is a schematic perspective view of a modified form of the invention.

FIG. 2 further shows details of vaporizer 17. A nozzle 54 is connected to tube 15 and has an electrical heater 56 connected thereto. The heater is of high wattage and heats the nozzle to a high temperature to cause the flash vaporization of solvent 18 which can then be removed either by evacuation or a purge gas thereby to carry the vapor away. The result is that any component 19 is directed as a collimated beam to form a spot 19C on the tape. Vaporizer 17 thus serves to remove the solvent or separate it from the sample component and to direct or spray the component as a collimated beam onto the tape. Such process is called "thermospraying". At periods of time when no component is within the effluent passing through vaporizer 17, no spot is formed on the tape and all of the solvent is vaporized and removed. Thermospraying works well when the sample is non-volatile, or where the molecular weight of a sample component is greater than that of the solvent.

The general operation of the system shown in FIG. 1 is as follows. Sample and solvent are introduced into LC 10 and the sample is separated into its components by an LC column 14. The effluent from column 14 is passed through vaporizer 17 which separates the solvent 18 from any component 19 and deposits the component as a spot on moving tape 20, at a first station located along the path of movement of the tape. The spots are then transported through a second station where the path of travel of tape 20 intercepts the optical path 32 of spectrometer 30. As each spot passes through the optical path, the movable mirror 35 of the interferometer makes at least one scan to allow a complete analysis to be made of the particular spot. Dependent upon the relative speeds of the tape and rates of scanning of mirror 35, multiple scans may be made on large size spots to increase any signal-to-noise ratio. Concurrently with the movement of the tape and spots thereon, the sprocket holes on the tape are counted to allow the location of any particular spot on the tape to be identified. At the end of the run, all of the tape may be then wound upon the take-up reel 22 and stored for later use. Obviously, the tape can be later used in conjunction with the spectrometer 30 in various ways. For example, an investigator might want to build up a weak signal associated with a given spot and so would cause the tape to be moved to where such spot is located in the optical path 32 whereupon further analysis can be made thereof. Alternatively, the same components can be deposited on the tape with no immediate analysis being made, and the analysis can be made later at the convenience of the investigator.

It should be obvious that those skilled in the art that many changes can be made in the details and arrangement of parts without departing from the scope of the invention defined in the appended claims.

Having thus described our invention, what we claim as new and desire to secure by Letters Patent is:

1. In a combined LC/FTIR system having an LC and an FTIR spectrometer, said LC effluxing an effluent comprising a solvent and separated sample components, said spectrometer comprising an IR detector and means for directing IR energy along an optical path terminating at said detector, the combination comprising:

a deposition media movable along a media path including first and second stations, said optical path traversing said media path at said second station; and thermospray means located at said first station, said thermospray means being connected to said LC to receive said solvent and said separated sample components, said thermospray means being operative to vaporize said solvent and to deposit said separated sample components at different locations and at different times on said media as it moves through said first station, whereby said separated components are non-destructively analyzed by said spectrometer as said media passes through said second station.

2. The combination of claim 1 wherein said deposition media is an elongated tape, and said combination further comprises:

tape transport means comprising a supply reel, a take-up reel, and a motor connected to one of said reels for moving said tape along a tape path extending through said first and second stations.

3. The combination of claim 2 wherein:
said tape is transparent to IR energy, and said optical path includes a portion at said second station wherein said IR energy is transmitted through said tape and any components thereon.

4. The combination of claim 2 wherein:
said tape is reflective of IR energy, and
said optical path includes a portion at said second station wherein said IR energy is reflected from a surface of said tape while being transmitted through any components deposited on such surface.

5. The combination of claim 2 wherein:
said tape comprises means for identifying the location of any said component deposited thereon.

* * * * *